United States Patent
Qin

(10) Patent No.: US 6,998,367 B2
(45) Date of Patent: Feb. 14, 2006

(54) ABSORBENT COMPOSITION CONTAINING TRANSITIONAL CROSSLINKING POINTS

(75) Inventor: Jian Qin, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 564 days.

(21) Appl. No.: 10/006,781

(22) Filed: Dec. 6, 2001

(65) Prior Publication Data

US 2003/0125684 A1 Jul. 3, 2003

(51) Int. Cl.
*B01J 20/00* (2006.01)

(52) U.S. Cl. .................. 502/400; 502/401; 502/402
(58) Field of Classification Search ................. 502/400, 502/401, 402
See application file for complete search history.

(56) References Cited

U.S. PATENT DOCUMENTS

| | | |
|---|---|---|
| 3,618,607 A | 11/1971 | Ells et al. |
| 3,939,123 A | 2/1976 | Matthews et al. |
| 4,043,952 A | 8/1977 | Ganslaw et al. |
| 4,090,013 A | 5/1978 | Ganslaw et al. |
| 4,548,847 A | 10/1985 | Aberson et al. |
| 4,698,404 A | 10/1987 | Cramm et al. |
| 4,783,510 A | 11/1988 | Saotome |
| 4,888,238 A | 12/1989 | Katz et al. |
| 4,910,250 A | 3/1990 | Saotome |
| 4,952,550 A | 8/1990 | Wallach et al. |
| 5,008,324 A | 4/1991 | Killgoar, Jr. et al. |
| 5,026,596 A | 6/1991 | Saotome |
| 5,071,681 A | 12/1991 | Manning et al. |
| 5,075,344 A | 12/1991 | Johnson |
| 5,126,382 A | 6/1992 | Hollenberg |
| 5,374,684 A | 12/1994 | Tai |
| 5,376,727 A | 12/1994 | Iqbal et al. |
| 5,422,330 A | 6/1995 | Kaylor |
| 5,470,964 A | 11/1995 | Qin |
| 5,508,381 A | 4/1996 | Jang et al. |
| 5,532,350 A | 7/1996 | Cottrell et al. |
| 5,550,189 A | 8/1996 | Qin et al. |
| 5,633,316 A | 5/1997 | Gartner et al. |
| 5,693,707 A | 12/1997 | Cheng et al. |
| 5,773,564 A | 6/1998 | Sikes |
| 5,801,116 A | 9/1998 | Cottrell et al. |
| 5,837,789 A | 11/1998 | Stockhausen et al. |
| 5,849,000 A | 12/1998 | Anjur et al. |
| 5,869,215 A | 2/1999 | Ong et al. |
| 5,886,120 A | 3/1999 | Tanaka et al. |
| 5,985,434 A | 11/1999 | Qin et al. |
| 6,084,045 A | 7/2000 | Fornasari et al. |
| 6,087,002 A | 7/2000 | Kimura et al. |
| 6,187,872 B1 | 2/2001 | Yanase et al. |
| 6,222,091 B1 | 4/2001 | Beihoffer et al. |
| 6,224,892 B1 | 5/2001 | Searle |
| 6,271,278 B1 | 8/2001 | Park et al. |
| 6,284,362 B1 | 9/2001 | Takai et al. |
| 6,284,367 B1 | 9/2001 | Gruhn et al. |
| 6,287,679 B1 | 9/2001 | Pappas et al. |
| 6,313,231 B1 | 11/2001 | Hosokawa et al. |
| 6,329,565 B1 | 12/2001 | Dutkiewicz et al. |
| 6,348,236 B1 | 2/2002 | Fairgrieve et al. |
| 2003/0018313 A1 | 1/2003 | Tanzer et al. |

FOREIGN PATENT DOCUMENTS

| | | |
|---|---|---|
| WO | WO 98/24832 | 6/1998 |
| WO | WO 01/87365 A2 | 11/2001 |

*Primary Examiner*—Stanley S. Silverman
*Assistant Examiner*—Edward M. Johnson
(74) *Attorney, Agent, or Firm*—Pauley Petersen & Erickson

(57) ABSTRACT

A water insoluble, water swellable absorbent composition exhibiting a free swell absorbency of at least 15 g/g and an Absorbency Change of greater than or equal to 15% upon saturation. The absorbent composition includes both permanent crosslinking points and transitional crosslinking points. The absorbent composition has a high free swell capacity as well as a high absorbency under load.

69 Claims, 2 Drawing Sheets

ABSORBENT COMPOSITION CONTAINING TRANSITIONAL CROSSLINKING POINTS

BACKGROUND OF THE INVENTION

This invention is directed to an absorbent composition containing transitional crosslinking points. There are two types of crosslinking points, conventional permanent crosslinking points and transitional crosslinking points. Permanent crosslinking points are those that exist in a polymer without undergoing a significant increase or decrease in their total numbers before, during, or after saline saturation. Transitional crosslinking points can either be pre-existing in a polymer and undergo a significant decrease in their total numbers after saline saturation, or can be established in a use situation and undergo a significant increase in their total numbers during or after saline saturation.

Superabsorbent materials used in current disposable diapers or other personal care products are generally a crosslinked highly water insoluble but swellable polyelectrolyte. For example, a high molecular weight sodium polyacrylate salt (Na—PA), crosslinked by either covalent bonds, such as —C—C—, —C—O—, —C—N—, or ionic bonds, such as $Al^{3+}$, $Zr^{4+}$, $Fe^{3+}$, $Cr^{3+}$, $Ti^{3+}$, or $Ce^{4+}$, can absorb more than 40 grams of 0.9% NaCl saline per gram of the polymer when no external pressure is applied on it, or more than 20 grams of the saline per gram of the polymer when a 0.3 pound per square inch pressure is applied on it. The absorbency without pressure on the polymer is the free swell capacity, and that with pressure on it is the absorbency under load (AUL).

In general, a polyelectrolyte, when crosslinked slightly, has a high free swell capacity but a low AUL value due to a low gel stiffness. On the other hand, a polyelectrolyte, when crosslinked heavily, has a lower free swell capacity but a higher AUL value. In order to have a maximum AUL value, current superabsorbent material has to sacrifice its free swell capacity. This is only true when the permanent crosslinking points are formed in the superabsorbent material. Though a high free swell but soft gel is not capable of absorbing liquid under pressure, it is capable of retaining huge amounts of liquid under pressure if the gel is allowed to swell first and then a load is applied.

Current commercially available superabsorbent materials are typically crosslinked by permanent crosslinking points by covalent bonds. It is known in the art to use metal ions ($Al^{3+}$ or $Zr^{4+}$) as either bulk or surface crosslinking agent. Within the same art, the addition of the metals ions into absorbent polymers is followed by a drying process. The drying process causes the resulting ionic bonds to be permanent crosslinks rather than transitional crosslinks.

Because conventional superabsorbent material is incapable of simultaneously possessing high free swell capacity and high AUL, it can be difficult to control the fluid absorption rate of the material. Furthermore, the process of making the superabsorbent material can be complicated due to the necessity of carrying out a surface crosslinking step or other modification processes in order to adjust the fluid absorption rate, fluid distribution, and fluid intake.

There is a need or desire for an absorbent material that can simultaneously possess high absorbent capacity and high absorbency under load.

SUMMARY OF THE INVENTION

In response to the discussed difficulties and problems encountered in the prior art, a new absorbent composition has been discovered.

The present invention is directed to a water insoluble, water swellable absorbent material exhibiting a high free swell absorbency and a high absorbency under load (AUL). The absorbent material is particularly suitable for use in absorbent garments, such as diapers, training pants, adult incontinence products and feminine care products.

The absorbent material is made up of superabsorbent material with both permanent crosslinking points and transitional crosslinking points or transitional crosslinker. As a result, the absorbent material of the invention has a free swell absorbency of at least 15 g/g and an Absorbency Change (the detailed definition of which refers to the Testing Method Section, below) of greater than or equal to 15% upon saturation due to increase or decrease in numbers of the transitional crosslinking points, while conventional superabsorbent material without the transitional crosslinking points exhibits such a change less than 10%.

Unlike the permanent crosslinking points which exist in a polymer without undergoing a significant increase or decrease in their total numbers before, during, or after saline saturation, the transitional crosslinking points can be either pre-existing in the polymer and then undergo a disassociation process upon use, or can be newly established in a use situation. Both increasing and decreasing numbers of transitional crosslinking points only occur in situ in an absorbent product when the absorbent composition is saturated by body fluids, such as urine. In the present invention, a superabsorbent material can be crosslinked to a first extent by permanent crosslinking points at which extent it is under-crosslinked and has a very high free swell capacity. The superabsorbent material can continue to be crosslinked to a second extent by a transitional crosslinker in situ in an absorbent product upon saturation at which extent it is well-crosslinked and has a very high AUL value. This absorbent composition contains formable transitional crosslinker. Alternatively, in a use situation, the superabsorbent material can exhibit a high AUL value contributed by both types of crosslinking points and then further resume a high free swell capacity upon saturation due to disassociation of those transitional crosslinking points by a transitional crosslinker removing agent. This second type of the absorbent composition contains removable transitional crosslinker.

Both the first and the second types of the transitional crosslinking agents can be used in many forms with the superabsorbent materials. For example, the transitional crosslinking agents can be in granular powder form which can be mixed with conventional superabsorbent material. As another example, the transitional crosslinking agents can be coated onto either superabsorbent material or other diaper components, such as liner, surge, fluff, or diaper backsheet. When a transitional crosslinking agent is mixed with a superabsorbent material, it is important that the transitional crosslinking agent is not reacting with (or crosslinking) the superabsorbent material. The two substances are only physically mixed together. No crosslinking points are formed between them. To prevent the transitional crosslinking agent from forming crosslinking points with the superabsorbent material, it is important to avoid any presence of water in the mixture or in mixing processes, such as coating, agglomerating, blending, encapsulating, etc. Water is capable of dissolving (or ionizing) the transitional crosslinking agent to trigger transitional crosslinking reaction. The absorbent composition comprising a superabsorbent material and a transitional crosslinker forming agent or a transitional crosslinker removing agent has to avoid any contact with any aqueous liquid in all preparation steps of absorbent composition production as well as absorbent product production.

Suitable polymers for the absorbent material of the invention include polyelectrolytes or polymers which are capable of being converted into polyelectrolytes through an in-situ neutralization or ion exchanging process. Examples of such polymers are (1) any anionic polymers and their respective polymers in acid forms; (2) any cationic polymers and their respective polymers in base forms; (3) mixtures of the above two types of polymers.

When an acidic, water swellable, water insoluble polymer is used, a basic neutralization agent is also used in order to achieve a high absorbency. The basic neutralization agent can be either a water-swellable, water-insoluble polymer or a non-polymer based organic or inorganic compound. When a basic, water-swellable, water-insoluble polymer is used, an acidic neutralization agent is also used in order to achieve a high absorbency. The acidic neutralization agent can be either a water-swellable, water-insoluble polymer or non-polymer based organic or inorganic compound.

The polymers mentioned above are crosslinked, using a permanent crosslinking agent, to an extent which provides the polymers with a high free swell capacity but a low AUL value. Suitable permanent crosslinking agents include, but are not limited to, (1) polymerizable crosslinking agents, such as methylene bisacrylamide; (2) reactive crosslinking agents, such as dialdehydes, or diepoxides; (3) latent crosslinking agents, such as an organic compound having at least two functional groups or functionalities capable of reacting with carboxyl (—COO$^-$), carboxylic acid (—COOH), amino (—NH$_2$), or hydroxyl (—OH) groups. Examples include, but are not limited to, diamines, polyamines, diols, polyols, dicarboxylic acid, polycarboxylic acid, and polyoxides. Another suitable crosslinking agent includes a metal ion with more than two positive charges, such as $Al^{3+}$, $Fe^{3+}$, $Ce^{3+}$, $Ce^{4+}$, $Ti^{4+}$, $Zr^{4+}$, and $Cr^{3+}$. In the case of cationic polymers, polyanionic substances are suitable crosslinking agents.

The ratio of permanent crosslinks to transitional crosslinks can be in a wide range dependent on overall required absorbency of the final superabsorbent material. If an extremely high free swell is required, a lower amount of the permanent crosslinks is needed. If an extremely high AUL and very firm swollen gel in the intended product are required, a higher amount of the permanent crosslinks is needed. Suitable ratios of the permanent crosslinks to the transitional crosslinks range from about 1:9 to about 9:1.

A considerable advantage of an absorbent material having both permanent crosslinks and transitional crosslinks is the capability of having both high free swell and high AUL. Furthermore, the absorptive properties of this material enables the material to provide a controlled fluid absorption rate as well as improved fluid distribution and intake. In addition, different crosslinking densities may be created in different zones of a diaper or other absorbent garment using just one superabsorbent. The absorbent composition of the invention may also simplify the superabsorbent process and reduce productions costs, for example by eliminating the surface crosslinking step or other modification processes. The absorbent composition may also provide more flexibility in product design, which may result in thinner products. Other potential benefits include improvements in gel stiffness and gel bed permeability.

With the foregoing in mind, particular embodiments of the invention provide a water insoluble, water swellable absorbent material exhibiting a high free swell absorbency and a high absorbency under load (AUL).

DEFINITIONS

Figure 1:
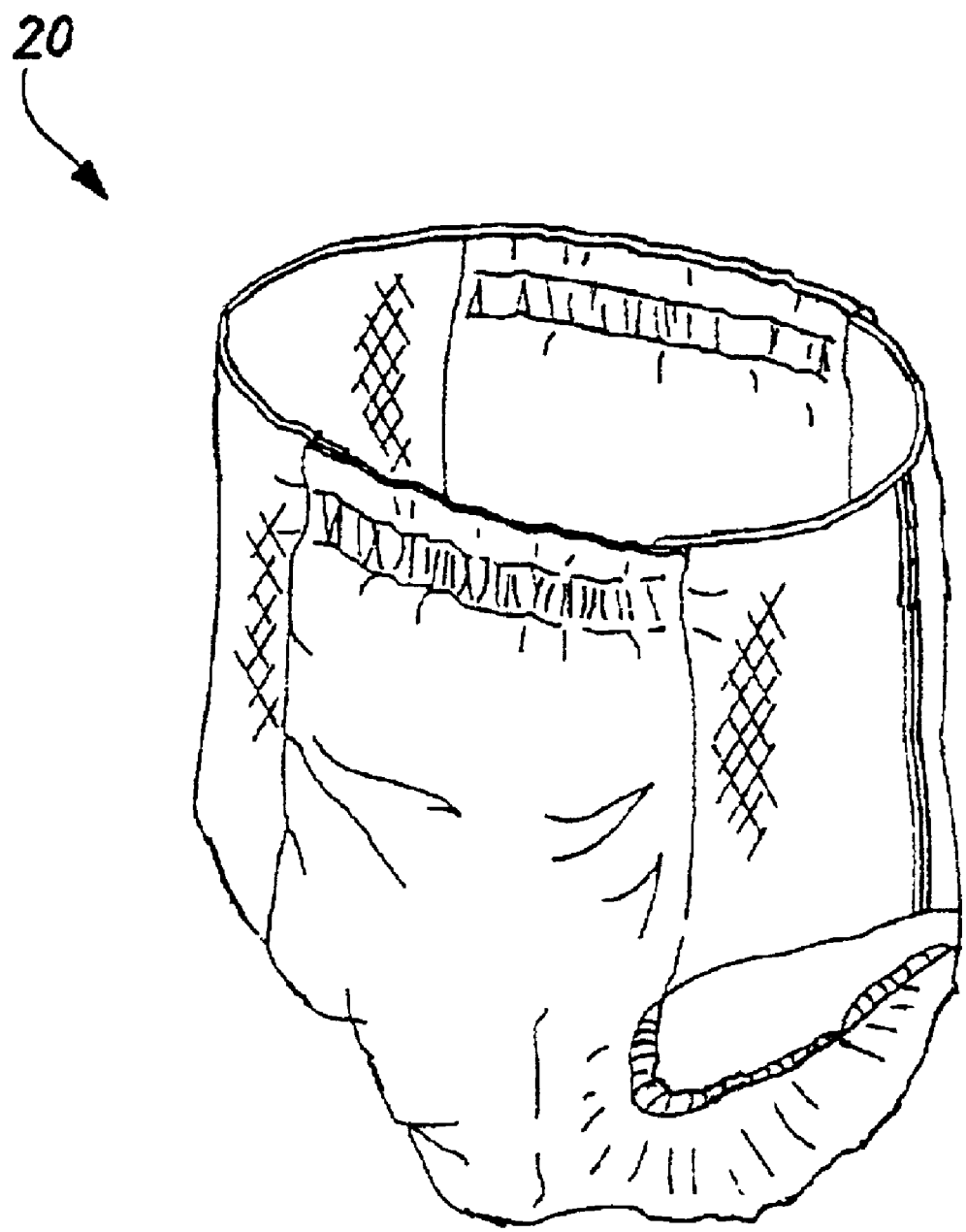
FIG. 1 is a perspective view of an absorbent garment containing the absorbent composition of the invention.

Within the context of this specification, each term or phrase below will include the following meaning or meanings.

"Absorbency under load" refers to the absorbency of a substance when a 0.3 pound per square inch pressure is applied to the substance.

"Free swell absorbency" or "free swell capacity" refers to the absorbency of a substance when no pressure is applied to the substance.

"Hydrolysable bonds" refers to bonds that can be broken by coming in contact with water, such as anhydrous bonds.

"In-situ reactive agent" refers to a chemical that reacts in a use situation, such as a chemical that can be mixed with another chemical in a dry state and upon saturation forms transitional crosslinking points.

"Latent crosslinking agent" refers to a reagent that does not crosslink a superabsorbent material in the process of polymerization and will crosslink it late when it is dried and proper conditions are provided. Such conditions include, but are not limited to, heat, microwave, electron beam, UV, any high energy radiations, high humidity, etc.

"Permanent crosslinking points" refers to crosslinking points that are present in a polymer and do not undergo a significant increase or decrease in the total number of such crosslinking points before, during, or after saline saturation.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Polymerizable crosslinking agent" refers to a reagent that contains more than one functional group that is polymerizable. For free radical polymerization, a reagent comprising more than one carbon-carbon double bond "C=C" is considered a polymerizable crosslinking agent, for example, methylene-bis-acrylamide.

"Reactive crosslinking agent" refers to a reagent that contains at least two functional groups capable of reacting with any pendant groups of a superabsorbent polymer. For example, when sodium polyacrylate is used, a reactive crosslinking agent can be chosen from a diol (butanediol) or a polyol (polyethylene glycol). A diol or a polyol forms ester linkages with carboxylic acid groups of the sodium polyacrylate. Such reactive crosslinking agent can also be chosen from a diamine (ethylene diamine) or a polyamine (chitosan). A diamine or a polyamine forms amide linkages with carboxylic acid groups of the sodium polyacrylate. Another example of such reactive crosslinking agent is a metal ion having at least three positive charges, i.e., $Al^{3+}$, $Zr^{4+}$, $Ce^{3+}$, $Ce^{4+}$, $Fe^{3+}$, to form ionic bonds with carboxyl groups (—COO$^-$) of the sodium polyacrylate.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Transitional crosslinking points" refer to crosslinking points that are either pre-existing in a polymer prior to saturation and undergo a significant decrease in the total number of such crosslinking points after saline saturation, or crosslinking points that are established in a use situation and also undergo a significant increase in the total number of such crosslinking points during or after saline saturation.

"Triggering disassociation bonds" refers to bonds that dissociate when triggered by a specific change in the environment surrounding the bond, such as those bonds sensitive to the changes in pH, ionic concentration, temperature, or moisture level.

"Triggering forming bond" refers to bonds that form when triggered by a specific change in the environment surrounding a polymer, such as those bonds sensitive to the changes in pH, ionic concentration, temperature, or moisture level.

"Water insoluble" refers to a material that does not dissolve when exposed to water.

"Water swellable" refers to a material that swells in size when exposed to water. Water swellable material generally retains its original identity or physical structure, but in a highly expanded state, during the absorption of the water and, thus, must have sufficient physical integrity to resist flow and fusion with neighboring particles.

"Weak bonds" refers to bonds that can be easily broken, such as hydrogen bonds, or macromolecular physical interaction.

These terms may be defined with additional language in the remaining portions of the specification.

DETAILED DESCRIPTION OF THE PRESENTLY PREFERRED EMBODIMENTS

The present invention is directed to a water swellable, water insoluble absorbent composition including either a superabsorbent material containing permanent crosslinking points and a transitional crosslinker, or a superabsorbent material containing permanent and transitional crosslinking points and a transitional crosslinker removing agent. Because of the presence of the transitional crosslinker or transitional crosslinker removing agent, the absorbent material has an absorbency under load (AUL) value of at least 10 g/g, or at least 15 g/g, or at least 20 g/g, and an Absorbency Change of greater than or equal to 15% upon saturation. Alternatively, the Absorbency Change may be at least 20% upon saturation, or at least 30% upon saturation. Furthermore, in addition to a high AUL, the absorbent material also possesses a high free swell absorbency of at least 15 g/g, or at least 20 g/g, or at least 25 g/g.

The absorbent material of the present invention is particularly suitable for use in disposable absorbent articles, such as diapers, training pants, incontinence products, other personal care or health care garments, including medical garments, or the like. An example of a training pant 20 including the absorbent material of the invention is shown in FIG. 1.

The absorbent material of the invention includes a superabsorbent material (SAM) with transitional crosslinking points and permanent crosslinking points. The permanent crosslinking points exist in a polymer without undergoing a significant increase or decrease in the total number of such crosslinking points before, during or after saline saturation. The transitional crosslinking points can either exist in a polymer and undergo a significant decrease in the total number of such crosslinking points after saline saturation, or can be established in a use situation and undergo a significant increase in the total number of such crosslinking points during or after saline saturation.

In one embodiment of the invention, the SAM can be crosslinked to a first extent by the permanent crosslinking points at which time the SAM is under-crosslinked and has a very high free swell capacity. This under-crosslinked SAM is then mixed with a formable transitional crosslinker to form the absorbent composition of this invention. The absorbent composition can continue to be crosslinked to a second extent by the transitional crosslinker when a bodily fluid, such s urine, is contacting the absorbent composition at which time the SAM is well-crosslinked and has a very high AUL value.

Suitable formable transitional crosslinks in this embodiment may include, but are not limited to, (1) in-situ reactive agents, such as metallic oxides, hydroxides, salts, and combinations of any of these, more specifically inorganic salts ($Al_2(SO_4)_3$, $Fe_2Cl_3$, $Ce(SO_4)_2$), ammonium zirconium carbonate (AZC), aluminum oxide ($Al_2O_3$), zirconium oxide, aluminum hydroxide ($Al[OH]_3$), aluminum chloride ($AlCl_3$), ceric ammonium sulfate ($Ce[NH_4]_4[SO_4]_4$), or organic compounds (dialdehydes, diepoxides, kymene, wet strength resins), these chemicals can be mixed with polyacrylate SAM in a dry (powder) state and in-situ form transitional crosslinking points upon saturation; (2) triggering forming bonds, such as bonds that are formed when triggered by the changes in pH, ionic concentration, temperature, or moisture level. The key criterion for such transitional crosslinks is that such bonds can not be formed before the polymer is saturated and must be able to form crosslinking points between polymer chains until the chains are fully swollen. If such crosslinking points are formed before the polymer starts to swell, the polymer can not achieve a high free swell capacity.

In another embodiment, the SAM can exhibit a high AUL value contributed by both types of crosslinking points, permanent and transitional, and then further achieve a high free swell capacity upon saturation due to disassociation of the transitional crosslinking points by a transitional crosslinker removing agent.

Suitable removable transitional crosslinks in this embodiment may include, but are not limited to, (1) weak bonds, such as hydrogen bonds or macromolecular physical interaction; (2) hydrolysable bonds, such as anhydrous bonds; or (3) triggering disassociation bonds, such as those bonds that dissociate when triggered by the changes in pH, ionic concentration, temperature, or moisture level. For example, when a metal ion (i.e., $Al^{3+}$) is used to crosslink a superabsorbent material, a chelating agent such as a phosphate (i.e., sodium phosphate) can be used to remove the $Al^{3+}$ ionic bonds between the superabsorbent polymer chains. The key criterion for such transitional crosslinks is that the bond has to be able to function as a crosslinking point until the neighboring molecular segments are fully swollen, and also has to be able to disassociate during use within a reasonable amount of time.

Suitable polymers for the SAM of this invention may include, but are not limited to, any polyelectrolytes or polymers which are capable of being converted into polyelectrolytes through an in-situ neutralization or ion exchanging process. Examples of such polymers are (1) any anionic polymers and their respective polymers in acid forms; (2) any cationic polymers and their respective polymers in base forms; (3) mixtures of the above two types of polymers.

Suitable anionic (or acidic), water-swellable, water-insoluble polymers include functional groups that are capable of generating or being converted to anions. Such functional groups include, but are not limited to, carboxyl groups, sulfonic groups, sulphate groups, sulfite groups, and phosphate groups. Suitably, the functional groups are carboxyl groups. Generally, the functional groups are attached to a crosslinked base polymer. Suitable base polymers include polyacrylates, polyacrylamides, polyvinyl alcohols, ethylene maleic anhydride copolymer, polyvinyl ethers, polyacrylamido methylpropane sulfonic acid, polyacrylic acids, polyvinylpyrrolidones, polyvinyl morpholines, and copolymers thereof. Natural based polysaccharide polymers may also be used, including carboxymethyl celluloses, carboxymethyl starches, acrylic grafted celluloses, hydrolyzed starch grafted polyacrylonitriles, and copolymers thereof. Synthetic polypeptides can also be used, such as polyaspartic acid and polyglutamic acid.

Suitable cationic (or basic), water-swellable, water-insoluble polymers include functional groups that are capable of generating or being converted to cations. Such functional groups include, but are not limited to, quaternary ammonium groups, primary, secondary, or tertiary amino groups, imino groups, imido groups, and amido groups. Suitably the functional groups are quaternary ammonium groups and primary amino groups. Generally, the functional groups are attached to a crosslinked base polymer. Suitable base polymers include polyamines, polyethyleneimines, polyacrylamides, polyvinylamines, polydiallyl dimethyl ammonium hydroxide, polyquaternary ammoniums, and copolymers thereof. Natural based polysaccharide polymers may also be used, including chitin and chitosan. Synthetic polypeptides can also be used, such as polyasparagins, polyglutamines, polylysines, and polyarginines.

When an acidic water swellable, water insoluble polymer is used, suitably at least about 50 molar percent, or at least about 70 molar percent, or at least about 90 molar percent, or substantially about 100 molar percent, of the acidic polymer's acidic functional groups are in free acid form. In order to achieve a high absorbency, a basic neutralization agent is used, which can be either a water-swellable, water-insoluble polymer or a non-polymer based organic or inorganic compound. Examples of suitable basic neutralization agents include, but are not limited to, polymeric basic materials such as polyamines, polyimines, polyamides, polyquaternary ammoniums, chitins, chitosans, polyasparagins, polyglutamines, polylysines, and polyarginines; organic basic materials such as organic salts, for example, sodium-citrate, and aliphatic and aromatic amines, imines, and amides; and inorganic bases such as metallic oxides, for example, calcium oxides; hydroxides, for example, barium hydroxide; salts such as sodium carbonate and sodium bicarbonate; and combinations of any of these.

When a basic, water-swellable, water-insoluble polymer is used, suitably at least about 50 molar percent, or at least about 70 molar percent, or at least about 90 molar percent, or substantially about 100 molar percent, of the basic polymer's basic functional groups are in free base form. In order to achieve a high absorbency, an acidic neutralization agent is used, which can be either a water-swellable, water-insoluble polymer or a non-polymer based organic or inorganic compound. Examples of suitable acidic neutralization agents include, but are not limited to, polymeric acidic materials such as polyacrylic acid, polymaleic acid, carboxymethyl cellulose, alginic acid, polyaspartic acid, and polyglutamic acid; organic acidic material such as aliphatic and aromatic acids, for example, citric acid, glutamic acid or aspartic acid; and inorganic acids such as metallic oxides, for example, aluminum oxide; and salts such as iron chloride, calcium chloride and zinc chloride; and combinations of any of these.

Any of the polymers mentioned above can be crosslinked using a permanent crosslinking agent to an extent which enables the polymer to have a high free swell capacity but a low AUL value. Suitable permanent crosslinking agents include, but are not limited to, polymerizable crosslinking agents, such as methylene bisacrylamide (MBA); reactive crosslinking agents, such as dialdehydes for example, glutaraldehyde, or diepoxides, for example polyethylene glycol diglycidyl ether; latent crosslinking agents, such as an organic compound having at least two functional groups or functionalities capable of reacting with carboxyl (—COO), carboxylic acid (—COOH), amino (—NH$_2$), or hydroxyl (—OH) groups. Examples of such suitable crosslinking agents include, but are not limited to, diamines, polyamines, diols, polyols, polycarboxylic acids, and polyoxides. Another suitable crosslinking agent includes a metal ion with at least three positive charges, such as $Al^{3+}$, $Fe^{3+}$, $Ce^{3+}$, $Ce^{4+}$, $Ti^{4+}$, $Zr^{4+}$, and $Cr^{3+}$. In the case of cationic polymers, polyanionic substances are suitable crosslinking agents. Examples are sodium polyacrylate, carboxymethylcellulose, and —$PO_4^{3-}$.

The water-swellable, water-insoluble polymer included in the absorbent composition may generally have a wide range of molecular weights. A water-swellable, water-insoluble polymer having a relatively high molecular weight can be beneficial for use in the present invention. Nonetheless, a wide range of molecular weights is generally suitable for use in the present invention. Water-swellable, water-insoluble polymers suitable for use in the present invention can suitably have a weight average molecular weight greater than about 100,000, and up to about 10,000,000. Methods of determining the molecular weight of a polymer are known to those skilled in the art.

The transitional crosslinking agents, described above, can be used in many forms with the superabsorbent materials. For example, the transitional crosslinking agents can be a granular powder, or other particulate form, and mixed with conventional superabsorbent material. In this case, the superabsorbent material and transitional crosslinking agent can be mixed either homogeneously or non-homogeneously (zoning). Homogeneous mixing is intended to achieve uniform blending of two particles. Each substance remains its own domain or phase. No molecular level mixing of the superabsorbent material and transitional crosslinking agent is achieved. In order to achieve the composition of this invention, it is important that two substances stay in their own phase before in-situ saturation triggers crosslinking reaction in an absorbent product. As another example, the transitional crosslinking agents can be coated, blended, printed, or encapsulated onto either superabsorbent material or other absorbent article components, such as a liner, a surge, fluff, or a backsheet (see FIG. 1).

The ratio of the permanent crosslinking points to the transitional crosslink points can be in a wide range dependent on overall required absorbency of the final superabsorbent material. If an extremely high free swell is desired, a lower amount of the permanent crosslinking points is used. If an extremely high AUL and very firm swollen gel in the resulting product are desired, a higher amount of the permanent crosslinking points is used. Suitably, the ratio of the permanent crosslinking points to the transitional crosslinking points is between about 1:9 and about 9:1, or between about 2:8 and about 8:2, or between about 3:7 and about 7:3.

As mentioned, the absorbent material of the invention suitably has a free swell absorbency of at least 15 g/g. The test method for determining free swell absorbency is described below. Additionally, the absorbent material of the invention suitably has an absorbency under load (AUL) value of at least 15 grams/gram. The test method for determining AUL is described below. Also previously mentioned, the absorbent material of the invention has an Absorbency Change of greater than or equal to 15% upon saturation due to an increase or decrease in numbers of the transitional crosslinking points. In comparison, conventional SAM without the transitional crosslinking points exhibits such a change less than 10%.

Conventional SAM is produced by synthesizing acrylate monomer in an aqueous solution and then drying the formed gel. The dried SAM is then ground into particulate form for use in an absorbent product. Such commercially available superabsorbents have little change in absorbency when they go through a re-wet and re-drying process due to lack of crosslinking point change. On the other hand, if the absorbent composition comprising a transitional crosslinking agent or a transitional crosslinker removing agent contacts water or water-containing liquid and then is dried before use in the absorbent product, the composition exhibits a huge change (either an increase or a decrease) in absorbency compared to current commercially available superabsorbent. The change comes from two reasons: (1) increase or decrease in overall crosslinking points due to formation or removal of transitional crosslinking points; or (2) transformation of transitional crosslinking points to permanent crosslinking points. The effect of permanent crosslinking points on absorbency is different from that of transitional crosslinking points.

In general, absorbency reduces when either type of crosslinking points increases. However, transitional crosslinking points have much less effect on absorbency than permanent crosslinking points. For example, when $Al^{3+}$ is used as a transitional crosslinker and mixed with sodium polyacrylate gel, the mixture exhibits a reasonably higher absorbency when it is saturated by saline, but a much lower absorbency when the mixture is exposed to water, dried and then saturated by saline. This is because the $Al^{3+}$ ions form transitional crosslinking points with sodium polyacrylate when the mixture is saturated once, while the ions form permanent crosslinking points when the mixture is re-saturated after being completely dried from the first saturation. The drying process converts transitional ionic crosslinking points into permanent crosslinking points. Therefore, we can measure Absorbency Change between once saturation and twice saturation to indicate existence of transitional crosslinking points. When Absorbency Change is greater than 15%, it indicates that absorbent composition contains transitional crosslinker or transitional crosslinker removing agent.

Examples provided below demonstrate the effect of transitional crosslinkers on AUL and free swell absorbency (Absorbency Under Zero Load—AUZL) values, as well as disassociation of transitional crosslinking points in a use situation, wicking properties of various superabsorbent materials within air laid superabsorbent/fluff compositions, and Absorbency Change data for a number of absorbent materials.

The presence of both permanent crosslinking points and transitional crosslinking points in the absorbent composition of the invention results in an absorbent material having both high free swell absorbency and high AUL. The absorbent composition also exhibits other benefits, including a controlled fluid absorption rate, as well as improved fluid distribution, intake, gel stiffness, and gel bed permeability. Furthermore, by applying the transitional crosslinking agent(s) in various densities among various zones of the SAM or SAM-containing composite having a certain degree of permanent crosslinking density, various densities of overall crosslinking points can be achieved within a single absorbent article using a single SAM.

EXAMPLES

Example 1

In order to form transitional crosslinking points in use, commercial superabsorbent from Hoechst Celanese, designated as IM 1000 P, a starch grafted crosslinked sodium salt of polyacrylic acid, was mixed with various amounts of a transitional crosslinker, ammonium zirconium carbonate (AZC) commercially available from Magnesium Elektron, Inc. Since the AZC was in solution form, it was pre-dissolved in 25 milliliters (ml) of 0.9 wt % NaCl test saline and then absorbency of the IM 1000 P in the saline was evaluated. Table 1 shows the absorbent properties of IM 1000 P and IM 1000 P/AZC. Without AZC, IM 1000 P has a very high Absorbency Under Zero Load (AUZL) but a very low AUL@0.3 psi value. Test methods for determining AUZL and AUL are described below. As can be seen from the results in Table 1, incorporation of transitional crosslinkers (AZC) significantly enhances AUL@0.3 psi and slightly reduces AUZL values.

TABLE 1

Absorbent Properties of IM 1000 P With Various Levels of AZC

| Absorbency Test | Amount of 40% AZC Solution Pre-Dissolved in 25 ml 0.9% NaCl Saline | | | | | |
|---|---|---|---|---|---|---|
| | 0 g | 0.05 g | 0.10 g | 0.20 g | 0.05 g | 1.00 g |
| AUZL (g/g) | 50.4 | 46.5 | 42.1 | 39.0 | 39.7 | 43.5 |
| AUL@0.3 psi (g/g) | 11.4 | 18.2 | 19.2 | 20.1 | 20.1 | 21.9 |

Example 2

In order to form transitional crosslinking points in use, IM 1000 P was mixed with various amounts of a solid transitional crosslinker, ceric ammonium sulfate (CAS: $Ce[NH_4]_4[SO_4]_4 \cdot 2H_2O$) commercially available from Mallinckrodt located in St. Louis, Mo., U.S.A. The mixtures were evaluated by AUZL and AUL@0.3 psi tests in 0.9% NaCl saline. Table 2 shows the results of the tests. Again, without CAS, IM 1000 P had very high AUZL values but very low AUL@0.3 psi values. As can be seen from the results in Table 2, incorporation of transitional crosslinkers (CAS) significantly enhances AUL@0.3 psi and slightly reduces AUZL values.

TABLE 2

Absorbent Properties of IM 1000 P With Various Levels of CAS

| Absorbency Test | Amount of Ce[NH$_4$]$_4$[SO$_4$]$_4$.2H$_2$O per gram of IM 1000 P | | | | | |
|---|---|---|---|---|---|---|
|  | 0 g | 0.0005 g | 0.001 g | 0.005 g | 0.01 g | 0.02 g |
| AUZL (g/g) | 50.2 | 45.3 | 44.6 | 40.2 | 37.4 | 34.7 |
| AUL@0.3 psi (g/g) | 11.4 | 11.3 | 10.9 | 13.7 | 19.5 | 23.8 |

Example 3

In order to demonstrate removal of transitional crosslinking points in use, 3.75 grams of 40% AZC solution were dissolved in 2000 grams of distilled water and 100 grams of IM 1000 P was added. The solution was stirred and all liquid was swollen by the IM 1000 P within a few minutes. The swollen IM 1000 P was dried in an oven at 60° C. overnight and the dried IM 1000 P was screened to 300 to 600 micron particles. The particles were heat treated at 200° C. for 4 hours. The heat cured IM 1000 P was tested both AUZL and AUL in a 0.9% NaCl saline containing different amounts of per-dissolved 1% Na$_3$PO$_4$ saline (Na$_3$PO$_4$ is pre-dissolved in 0.9% NaCl saline at a weight ratio of 1 to 99). Two commercial superabsorbent materials, IM 1000 P and Favor 880, available from Stockhausen Inc., were used as controls for these tests. Table 3 summarizes the results of this study.

As can be seen from the results in table, transitional crosslinker removing agent, Na$_3$PO$_4$, removes Zr$^{4+}$ ionic transitional crosslinking points to enhance absorbency, while Na$_3$PO$_4$ reduces conventional SAM's absorbency due to higher concentration of salt effect.

TABLE 3

Absorbent Properties of AZC Crosslinked IM 1000 P with Various Levels of Na$_3$PO$_4$

| SAM | Transitional Crosslinker | Absorbency Test | Amount (gram) of 1% Na$_3$PO$_4$ in 15 ml Saline | | | | | |
|---|---|---|---|---|---|---|---|---|
|  |  |  | 0 | 0.25 | 0.50 | 0.75 | 1.00 | 1.50 |
| IM 1000 P | None | AUZL | 50.2 | 46.7 | — | 46.3 |  | 46.5 |
|  |  | AUL | 11.4 | 10.0 | — | 8.6 |  | 8.7 |
| IM 1000 P | 1.5% AZC | AUZL | 28.4 | 28.3 | 29.3 | 30.7 | 31.5 | 32.6 |
|  |  | AUL | 24.1 | 23.9 | 23.9 | 24.9 | 25.8 | 26.1 |
| Favor 880 | None | AUZL | 31.4 | 27.5 | — | 28.3 |  | 27.8 |
|  |  | AUL | 29.8 | 25.9 | — | 24.8 |  | 24.8 |

Example 4

In order to disassociate transitional crosslinking points in use, 27 grams (g) of acrylic acid, 0.065 g of K$_2$S$_2$O$_8$, 0.108 g of N,N'-methylene bis-acrylamide (MBA) and 175 g of distilled water were added to a 500 ml flask and mixed at room temperature to form a completely dissolved solution. The flask was then immersed into a water bath at 60° Celsius for several hours and constantly shaken inside the bath. Polyacrylic acid gel formed and was cut into ¼-inch cubes and added into a pre-prepared solution having 7.5 g of NaOH and 500 g of water. The polyacrylic acid gel after this step had a degree of neutralization of about 50 molar percentage and was then dried at 80° Celsius and ground into particles. The particles were heated at 160 to 200° Celsius to induce anhydride linkages between carboxylic acid groups as transitional crosslinks. The particles were mixed with sodium bicarbonate powder at a weight ratio of 1 gram of the polymer to 0.23 or 0.46 gram of bicarbonate. The additional bicarbonate brought the total degree of neutralization to 70% or 90% and also may have provided a slightly basic condition which may have helped disassociation of anhydride linkages. The absorbent properties of the treated polymer were evaluated in 0.9% NaCl saline. Table 4 shows the results of the tests (absorbency data were measured for 10 hours).

TABLE 4

Absorbent Properties of Treated Polymer

| Degree of Neutralization of Polyacrylate Gel | PAA/NaHCO$_3$ (g/g) | Heat Treatment (° C./min) | AUZL (g/g) | AUL@0.3 psi (g/g) |
|---|---|---|---|---|
| 70% | 1/0.23 | Non-Heated | 39.2 | 10.5 |
|  |  | 200/60 | 40.5 | 13.2 |
|  |  | 200/120 | 40.1 | 14.1 |
| 90% | 1/0.46 | Non-Heated | 50.8 | 12.3 |
|  |  | 160/240 | 50.6 | 17.8 |
|  |  | 200/60 | 51.2 | 18.6 |
|  |  | 200/120 | 50.4 | 19.2 |

Example 5

Air laid superabsorbent/fluff composites, including 37% superabsorbent powder and 63% wood pulp fluff and having a total basis weight of 500 grams per square meter (gsm), were made using both current commercial superabsorbent Favor 880, available from Stockhausen GmbH & Co. located in Krefeld, Fed. Rep. of Germany, and the past commercial superabsorbent IM 1000 P, and a wood pulp fluff commercially available from U.S. Alliance, Childersburg, Ala., U.S.A., under the trade designation CR1654. The composites were densified to a density of about 0.2 g/cc. An inclined wicking test (refer to European Patent 0 532 002 A1 for detailed information in Inclined Wicking Test) was performed on the densified composites (inclined angle: 30°, testing time: 1 hour, 30 minutes). Both wicking distance and capacity were recorded as parameters to characterize wicking properties. Results are shown in Table 5.

TABLE 5

Wicking Properties of Air Laid Superabsorbent/Fluff Composites

| Composition | Testing Fluid | Wicking Distance (cm) | Wicking Capacity (g/g) |
|---|---|---|---|
| 37% IM 1000 P/ 63% CR1654 | 0.9% NaCl | 12.1 | 8.3 |
| 37% IM 1000 P/ 63% CR1654 | 0.9% NaCl/AZC* | 19.6 | 13.5 |
| 37% Favor 880/ 63% CR1654 | 0.9% NaCl | 21.5 | 12.5 |

*AZC is pre-dissolved in 0.9% NaCl saline at a ratio of 0.5 g of 40% AZC to 25 ml of 0.9% NaCl saline

Example 6

In order to demonstrate that an absorbent composition comprising transitional crosslinking points exhibits a greater Absorbency Change than that comprising only permanent crosslinking points, both conventional superabsorbent materials (DRYTECH 2035, commercially available from Dow Chemical Co., Midland, Mich., U.S.A.) and absorbent compositions of this invention were selected and their Absorbency Change values were measured in accordance with the test methods described below. The results are shown in Table 6. As can be seen from the results in Table 6, absorbent compositions comprising either formable or removable transitional crosslinking points all exhibit an Absorbency Change value in either AUZL or AUL greater than 15%.

bency Under Zero Load and Absorbency Under 0.3 psi Load are used to evaluate Absorbency Change before and after the treatment. It is believed that the permanent crosslinking points should have a little change but the transitional crosslinking points should have a huge change upon the above treatment (either formed or removed).

The amount of transitional crosslinks can be quantified by Absorbency Change value. Absorbency Change is the absorbency change upon saturation, and can be defined by percentage increase or decrease in either AUZL or AUL values of a superabsorbent before and after the treatment described above in this test method. The higher the Absorbency Change (either increase or decrease), the more transitional crosslinking points the superabsorbent has.

TABLE 6

Absorbency Change Data

| Superabsorbent/Transitional Crosslinker/Removing Agent | Absorbency (g/g) Before Treatment | | Absorbency (g/g) After Treatment | | Absorbency Change (%) | |
|---|---|---|---|---|---|---|
| | AUZL | AUL@ 0.3 psi | AUZL | AUL@ 0.3 psi | AUZL | AUL @ 0.3 psi |
| * Favor 880 | 31.4 | 29.8 | 33.6 | 27.4 | +7.0 | −8.1 |
| * Drytech 2035 | 29.5 | 28.6 | 30.2 | 26.5 | +2.4 | −7.3 |
| * IM 1000 P | 50.4 | 11.4 | 48.6 | 10.9 | −3.6 | −4.4 |
| IM 1000 P/40% AZC | 39.7 | 20.1 | 15.4 | 12.8 | −61.2 | −36.3 |
| IM 1000 P/9% AlCl$_3$ | 38.3 | 23.2 | 14.2 | 13.6 | −62.9 | −41.4 |
| IM 1000 P/6% Ce[NH$_4$]$_4$[SO$_4$]$_4$ | 37.4 | 19.5 | 13.2 | 10.1 | −64.7 | −48.2 |
| IM 1000 P/1.5% AZC & 200° C. for 4 hours/6% Na$_3$PO$_4$ | 31.5 | 25.8 | 45.6 | 15.2 | +44.8 | −41.1 |
| * PAA-NaHCO$_3$/Unheated | 50.8 | 12.3 | 50.1 | 11.9 | −1.4 | −3.3 |
| PAA-NaHCO$_3$/200° C. for 2 hours | 50.4 | 19.2 | 49.8 | 13.2 | −1.2 | −31.3 |

Note: * Not an example of this invention

Test Method for Determining Transitional Crosslinks and Absorbency Change

Place 10 grams of an absorbent composition comprising a superabsorbent material (either conventional SAM or the SAM having either formable or removable transitional crosslinks) in a 500 ml beaker and add 250 grams of distilled water with agitation. After the superabsorbent absorbs all the water, dry the superabsorbent in an oven at 50° Celsius until the superabsorbent is completely dry. Grind the dried superabsorbent into particles. The particles having 300 to 600 microns are used to evaluate absorbent properties. Absor-

Test Method for Determining Absorbency Under Load (AUL)

Figure 2:
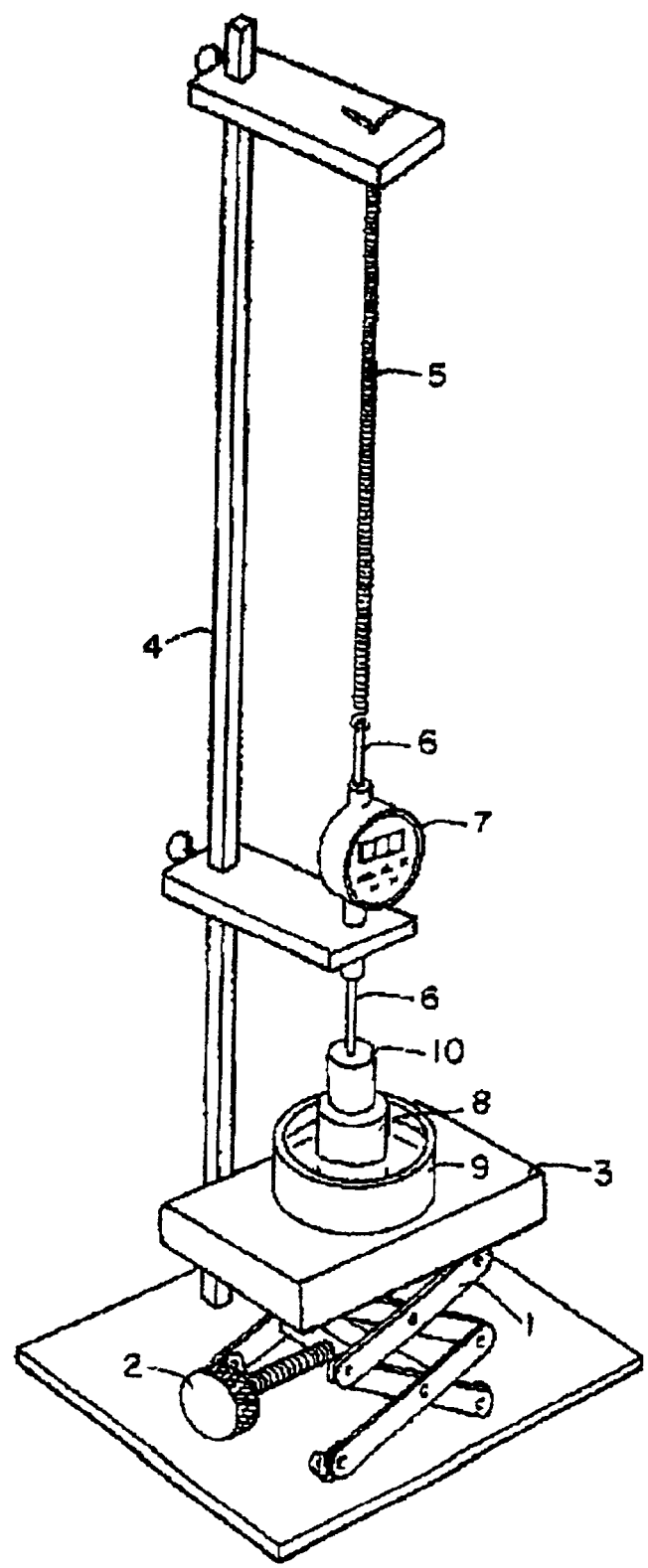
FIG. 2 illustrates the apparatus for determining the Absorbency Under Load values of an absorbent material.

The Absorbency Under Load (AUL) is a test which measures the ability of an absorbent material to absorb a liquid (such as a 0.9 weight percent solution of sodium chloride in distilled water) while under an applied load or restraining force. Referring to FIG. 2, the apparatus and method for determining AUL will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9, which contains the saline solution to be absorbed and optionally transitional crosslinker or removing agent. A weight 10 rests on top of a spacer disc (not visible) resting on top of the superabsorbent material sample (not visible).

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shi-ba 5-chome, Minatoku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill. Item No. 9640K41), which serves to counter or reduce the downward force of the probe to about 1 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 gram weight is then placed on top of the spacer disc, thereby applying a load of about 0.3 pound per square inch. The sample cup is placed in the Petri dish on the platform and the laboratory jack raised up until it contacts the tip of the probe. The meter is zeroed. A sufficient amount of saline solution is added to the Petri dish (15–25 milliliters) to begin the test. The distance the weight 10 is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after about 60 minutes is the AUL value expressed as grams saline solution absorbed per gram of absorbent. If desired, the readings of the modified thickness meter can be continuously inputted to a computer (Mitutoyo Digimatic Miniprocessor DP-2 DX) to make the calculations and provide AUL readings. As a cross-check, the AUL can also be determined by determining the weight difference between the sample cup before and after the test, the weight difference being the amount of solution absorbed by the sample.

Test Method for Determing Absorbency Under Zero Load (AUZL)

The same procedure used for determining AUL, described above, is used to determine AUZL, except that no 100 gram weight (item 10 in FIG. 2) is used. AUZL is used in this invention to represent free swell capacity of an absorbent composition.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent composition comprising:
   a superabsorbent material having a plurality of permanent crosslinking points and a plurality of transitional crosslinking points, the superabsorbent material exhibiting a free swell absorbency of at least 15 g/g and an Absorbency Change of at least 15% upon saturation.

2. The absorbent composition of claim 1, wherein the superabsorbent material exhibits an Absorbency Change of at least 20% upon saturation.

3. The absorbent composition of claim 1, wherein the superabsorbent material exhibits an Absorbency Change of at least 30% upon saturation.

4. The absorbent composition of claim 1, wherein the superabsorbent material exhibits a free swell absorbency of at least 20 grams/gram.

5. The absorbent composition of claim 1, wherein the superabsorbent material exhibits a free swell absorbency of at least 25 grams /gram.

6. The absorbent composition of claim 1, wherein the superabsorbent material has an absorbency under load value of at least 10 grams/gram.

7. The absorbent composition of claim 1, wherein the superabsorbent material has an absorbency under load value of at least 15 grams/gram.

8. The absorbent composition of claim 1, wherein the superabsorbent material has an absorbency under load value of at least 20 grams/gram.

9. The absorbent composition of claim 1, wherein the plurality of transitional crosslinking points are pre-existing in the superabsorbent material and undergo a disassociation process upon saturation.

10. The absorbent composition of claim 9, wherein the plurality of transitional crosslinking points comprises weak bonds.

11. The absorbent composition of claim 9, wherein the plurality of transitional crosslinking points comprises hydrolysable bonds.

12. The absorbent composition of claim 9, wherein the plurality of transitional crosslinking points comprises triggering disassociation bonds.

13. The absorbent composition of claim 9, wherein the plurality of transitional crosslinking points comprises a plurality of ionic bonds that are disassociated by a removing agent.

14. The absorbent composition of claim 13, wherein the ionic bonds are formed by metal ions having at least three positive charges.

15. The absorbent composition of claim 13, therein the removing agent comprises a chelating agent.

16. The absorbent composition of claim 15, wherein the chelating agent comprises sodium phosphate.

17. The absorbent composition of claim 1, wherein the plurality of transitional crosslinking points are newly established upon use subsequent to saturation of the superabsorbent material.

18. The absorbent composition of claim 17, wherein the plurality of transitional crosslinking points comprises a plurality of in-situ reactive agents that can be mixed with polyacrylate superabsorbent material in a dry state and in-situ form transitional crosslinking points upon saturation.

19. The absorbent composition of claim 18, wherein the plurality of in-situ reactive agents comprise a dry powder selected from the group consisting of metallic oxides, hydroxides, salts, and combinations thereof.

20. The absorbent composition of claim 18, wherein the plurality of in-situ reactive agents comprise a dry powder selected from the group consisting of aluminum oxide, zirconium oxide, aluminum hydroxide, aluminum chloride, ammonium zirconium carbonate, aluminum sulfate, ceric ammonium sulfate, and combinations thereof.

21. The absorbent composition of claim 17, wherein the plurality of transitional crosslinking points comprises triggering forming bonds.

22. The absorbent composition of claim 1, wherein the absorbent composition can be integrated with a component of an absorbent article using a method selected from the group consisting of blending, printing, coating, and encapsulating.

23. The absorbent composition of claim 1, wherein the superabsorbent material and the plurality of transitional crosslinking points are homogeneously incorporated into the absorbent composition.

24. The absorbent composition of claim 1, wherein the superabsorbent material and the plurality of transitional crosslinking points are non-homogeneously incorporated into the absorbent composition.

25. The absorbent composition of claim 1, wherein the superabsorbent material comprises an acidic, water-swellable, water insoluble polymer having at least about 50 molar percent of its acidic functional groups in free acid form, and a basic neutralization agent.

26. The absorbent composition of claim 1, wherein the superabsorbent material comprises a basic, water-swellable, water insoluble polymer having at least about 50 molar percent of its basic functional groups in free base form, and an acidic neutralization agent.

27. The absorbent composition of claim 26, wherein the plurality of permanent crosslinking points are formed by a polyanionic crosslinking agent.

28. The absorbent composition of claim 1, wherein the superabsorbent material comprises an acidic, water-swellable, water-insoluble polymer having at least about 50 molar percent of its acidic functional groups in free acid form; and a basic, water-swellable, water-insoluble polymer having at least about 50 molar percent of its basic functional groups in free base form.

29. The absorbent composition of claim 1, wherein the plurality of permanent crosslinking points are formed by a polymerizable crosslinking agent.

30. The absorbent composition of claim 29, wherein the polymerizable crosslinking agent comprises methylene bisacrylamide.

31. The absorbent composition of claim 1, wherein the plurality of permanent crosslinking points are formed by a reactive crosslinking agent selected from the group consisting of dialdehydes and diepoxides.

32. The absorbent composition of claim 31, wherein the reactive crosslinking agent is selected from the group consisting of glutaraldehyde and polyethylene glycol diglycidyl ether.

33. The absorbent composition of claim 1, wherein the plurality of permanent crosslinking points are formed by a latent crosslinking agent.

34. The absorbent composition of claim 33, wherein the latent crosslinking agent comprises an organic compound having at least two functionalities capable of reacting with at least one functional group selected from the group consisting of carboxyl, carboxylic acid, amino, and hydroxyl groups.

35. The absorbent composition of claim 34, wherein the latent crosslinking agent comprises an organic compound selected from the group consisting of diamines, polyamines, diols, polyols, polycarboxylic acids, and polyoxides.

36. The absorbent composition of claim 1, wherein the plurality of permanent crosslinking points are formed by a crosslinking agent having a metal ion with more than two positive charges.

37. The absorbent composition of claim 36, wherein the metal ion in the crosslinking agent is selected from the group consisting of $Al^{3+}$, $Fe^{3+}$, $Ce^{3+}$, $Ce^{4+}$, $Ti^{4+}$, $Zr^{4+}$, and $Cr^{3+}$.

38. The absorbent composition of claim 1, wherein the permanent crosslinking points and the transitional crosslinking points are present in the superabsorbent material in a ratio of between 1:9 and 9:1.

39. The absorbent composition of claim 1, wherein the permanent crosslinking points and the transitional crosslinking points are present in the superabsorbent material in a ratio of between 2:8 and 8:2.

40. The absorbent composition of claim 1, wherein the permanent crosslinking points and the transitional crosslinking points are present in the superabsorbent material in a ratio of between 3:7 and 7:3.

41. An absorbent garment comprising the absorbent composition of claim 1.

42. The absorbent garment of claim 41, wherein a density of the permanent crosslinking points and the transitional crosslinking points varies throughout the absorbent composition.

43. An absorbent composition comprising:
an acidic, water-swellable, water insoluble polymer having at least about 50 molar percent of its acidic functional groups in free acid form; and
a basic neutralization agent;
wherein the absorbent composition exhibits a free swell absorbency of at least 15 g/g and an Absorbency Change of greater than or equal to 15% upon saturation.

44. The absorbent composition of claim 43, wherein the acidic, water-swellable, water insoluble polymer comprises at least one functional group selected from the group consisting of carboxyl groups, sulfonic groups, sulphate groups, sulfite groups, and phosphate groups.

45. The absorbent composition of claim 44, wherein the at least one functional group is attached to a crosslinked base polymer.

46. The absorbent composition of claim 45, wherein the crosslinked base polymer is selected from the group consisting of polyacrylates, polyacrylamides, polyvinyl alcohols, ethylene maleic anhydride copolymer, polyvinyl ethers, polyacrylamido methylpropane sulfonic acid, polyacrylic acids, polyvinylpyrrolidones, polyvinyl morpholines, and copolymers thereof.

47. The absorbent composition of claim 43, wherein the acidic, water-swellable, water insoluble polymer comprises a natural based polysaccharide polymer selected from the group consisting of carboxymethyl celluloses, carboxymethyl starches, acrylic grafted celluloses, hydrolyzed starch grafted polyacrylonitriles, and copolymers thereof.

48. The absorbent composition of claim 43, wherein the acidic, water-swellable, water insoluble polymer comprises a synthetic polypeptide selected from the group consisting of polyaspartic acid and polyglutamic acid.

49. The absorbent composition of claim 43, wherein the basic neutralization agent comprises a polymeric basic material selected from the group consisting of polyamines, polyimines, polyamides, polyquaternary ammoniums, chitins, chitosans, polyasparagins, polyglutamines, polylysines, and polyarginines.

50. The absorbent composition of claim 43, wherein the basic neutralization agent comprises an organic basic material selected from the group consisting of organic salts, aliphatic amines, aromatic amines, imines, and amides.

51. The absorbent composition of claim 43, wherein the basic neutralization agent comprises an inorganic basic material selected from the group consisting of metallic oxides, hydroxides, salts, and combinations thereof.

52. The absorbent composition of claim 43, wherein the acidic, water-swellable, water insoluble polymer has at least about 70 molar percent of its acidic functional groups in free acid form.

53. The absorbent composition of claim 43, wherein the acidic, water-swellable, water insoluble polymer has at least about 90 molar percent of its acidic functional groups in free acid form.

54. The absorbent composition of claim 43, wherein the acidic, water-swellable, water insoluble polymer has about 100 molar percent of its acidic functional groups in free acid form.

55. An absorbent composition comprising:
a basic, water-swellable, water insoluble polymer having at least about 50 molar percent of its basic functional groups in free base form; and
an acidic neutralization agent;
wherein the absorbent composition exhibits a free swell absorbency of at least 15 g/g and an Absorbency Change of greater than or equal to 15% upon saturation.

56. The absorbent composition of claim 55, wherein the basic, water-swellable, water insoluble polymer comprises at least one functional group selected from the group consisting of quaternary ammonium groups, primary amino groups, secondary amino groups, tertiary amino groups, imino groups, imido groups, and amido groups.

57. The absorbent composition of claim 56, wherein the at least one functional group is attached to a crosslinked base polymer.

58. The absorbent composition of claim 57, wherein the crosslinked base polymer is selected from the group consisting of polyamines, polyethyleneimines, polyacrylamides, polyvinylamines, polydiallyl dimethyl ammonium hydroxide, polyquaternary ammoniums, and copolymers thereof.

59. The absorbent composition of claim 55, wherein the basic, water-swellable, water insoluble polymer comprises a natural based polysaccharide polymer selected from the group consisting of chitin and chitosan.

60. The absorbent composition of claim 55, wherein the basic, water-swellable, water insoluble polymer comprises a synthetic polypeptide selected from the group consisting of polyasparagins, polyglutamines, polylysines, and polyarginines.

61. The absorbent composition of claim 55, wherein the acidic neutralization agent comprises a polymeric acidic material selected from the group consisting of polyacrylic acid, polymaleic acid, carboxymethyl cellulose, alginic acid, polyaspartic acid, and polyglutamic acid.

62. The absorbent composition of claim 55, wherein the acidic neutralization agent comprises an organic acidic material selected from the group consisting of aliphatic acids and aromatic acids.

63. The absorbent composition of claim 55, wherein the acidic neutralization agent comprises an organic acidic material selected from the group consisting of citric acid, glutamic acid, and aspartic acid.

64. The absorbent composition of claim 55, wherein the acidic neutralization agent comprises an inorganic acidic material selected from the group consisting of metallic oxides, salts, and combinations thereof.

65. The absorbent composition of claim 55, wherein the acidic neutralization agent comprises an inorganic acidic salt selected from the group consisting of iron chloride, calcium chloride, zinc chloride, and combinations thereof.

66. The absorbent composition of claim 55, wherein the basic, water-swellable, water insoluble polymer has at least about 70 molar percent of its basic functional groups in free base form.

67. The absorbent composition of claim 55, wherein the basic, water-swellable, water insoluble polymer has at least about 90 molar percent of its basic functional groups in free base form.

68. The absorbent composition of claim 55, wherein the basic, water-swellable, water insoluble polymer has about 100 molar percent of its basic functional groups in free base form.

69. The absorbent composition of claim 43, wherein addition of the basic neutralization agent to the acidic, water-swellable, water insoluble polymer results in a total degree of neutralization of 70% to 90%.

* * * * *